United States Patent [19]

Becker

[11] Patent Number: 5,648,821

[45] Date of Patent: Jul. 15, 1997

[54] REMOTE CURSOR CONTROL APPARATUS

[76] Inventor: Ricky C. Becker, 916 N. 39th St., Grand Forks, N. Dak. 58203

[21] Appl. No.: 128,862

[22] Filed: Sep. 29, 1993

[51] Int. Cl.$^6$ ............................................. H04N 05/945
[52] U.S. Cl. ............................ 348/601; 345/161; 348/45
[58] Field of Search ................................. 358/98; 348/45, 348/601; 345/161

[56] References Cited

U.S. PATENT DOCUMENTS 3,911,419  10/1975  Bates et al. ............................ 348/601
5,107,844   4/1992  Kami et al. ............................ 348/45

*Primary Examiner*—John K. Peng
*Assistant Examiner*—Nathan J. Flynn
*Attorney, Agent, or Firm*—Zarley, McKee, Thomte Voorhees & Sease; Mark D. Frederiksen

[57] ABSTRACT

A cursor control apparatus includes an operable control mounted on a housing for moving a cursor depicted on a video monitor. In one embodiment of the invention, the control and housing is formed of components which may be sterilized without affecting the mechanical and electrical properties of the apparatus. In a second embodiment, a sterilizable flexible and resilient covering covers the top portion of the housing and encases the operable control. The cursor control housing is provided with apparatus for securing the housing to the drape utilized to cover a patient in surgery.

13 Claims, 4 Drawing Sheets

REMOTE CURSOR CONTROL APPARATUS

TECHNICAL FIELD

The present invention relates generally to control apparatus for operating a cursor overlaid on a video image on a video screen, and more particular to a joystick control modified for a surgical environment.

BACKGROUND OF THE INVENTION

Endoscopic surgery is an area of surgery growing with staggering velocity. During such surgery, a camera and fiberoptics are utilized in combination with a myriad of modified tools, so as to make the procedure only minimally invasive. New procedures for such surgery are being rapidly developed and tested currently in the field.

While performing endoscopic surgery, the entire procedure is viewed from two video monitors. While conventional "open" surgery permits direct inspection and handling of organs and tissues, endoscopic surgery enables viewing only through the screen of the video monitor. For this reason, instructions and descriptions of the surgical field require either lengthy verbal descriptions or direct pointing at the video screen.

Verbal instructions are typically slow and inaccurate, especially in the teaching environment. Often, directions must be repeated frequently, such as "up, down, more to the right" etc. While pointing to the screen is quicker, and more accurate, the inventor has discovered that bacteria is transferred from the screen to the surgeon's glove by virtue of static electricity, even if the screen is not directly contacted. While the remainder of the surgical environment is sterile, the video screens are not, and the surgeon's gloves would then become contaminated.

SUMMARY OF THE INVENTION

It is therefore a general object of the present invention to provide an improved apparatus for controlling a cursor on a video screen in a surgical environment.

Another object of the present invention is to provide a cursor control apparatus which is selectively securable in an operating environment to permit one handed operation.

Still another object is to provide a cursor control apparatus which may be sterilized for use within the surgical environment.

These and other objects will be apparent to those skilled in the art.

The cursor control apparatus of the present invention includes an operable control mounted on a housing for moving a cursor depicted on a video monitor. In one embodiment of the invention, the control and housing is formed of components which may be sterilized without affecting the mechanical and electrical properties of the apparatus. In a second embodiment, a sterilizable flexible and resilient covering covers the top portion of the housing and encases the operable control. The cursor control housing is provided with apparatus for securing the housing to the drape utilized to cover a patient in surgery.

DESCRIPTION OF THE PREFERRED EMBODIMENTS

Figure 1:
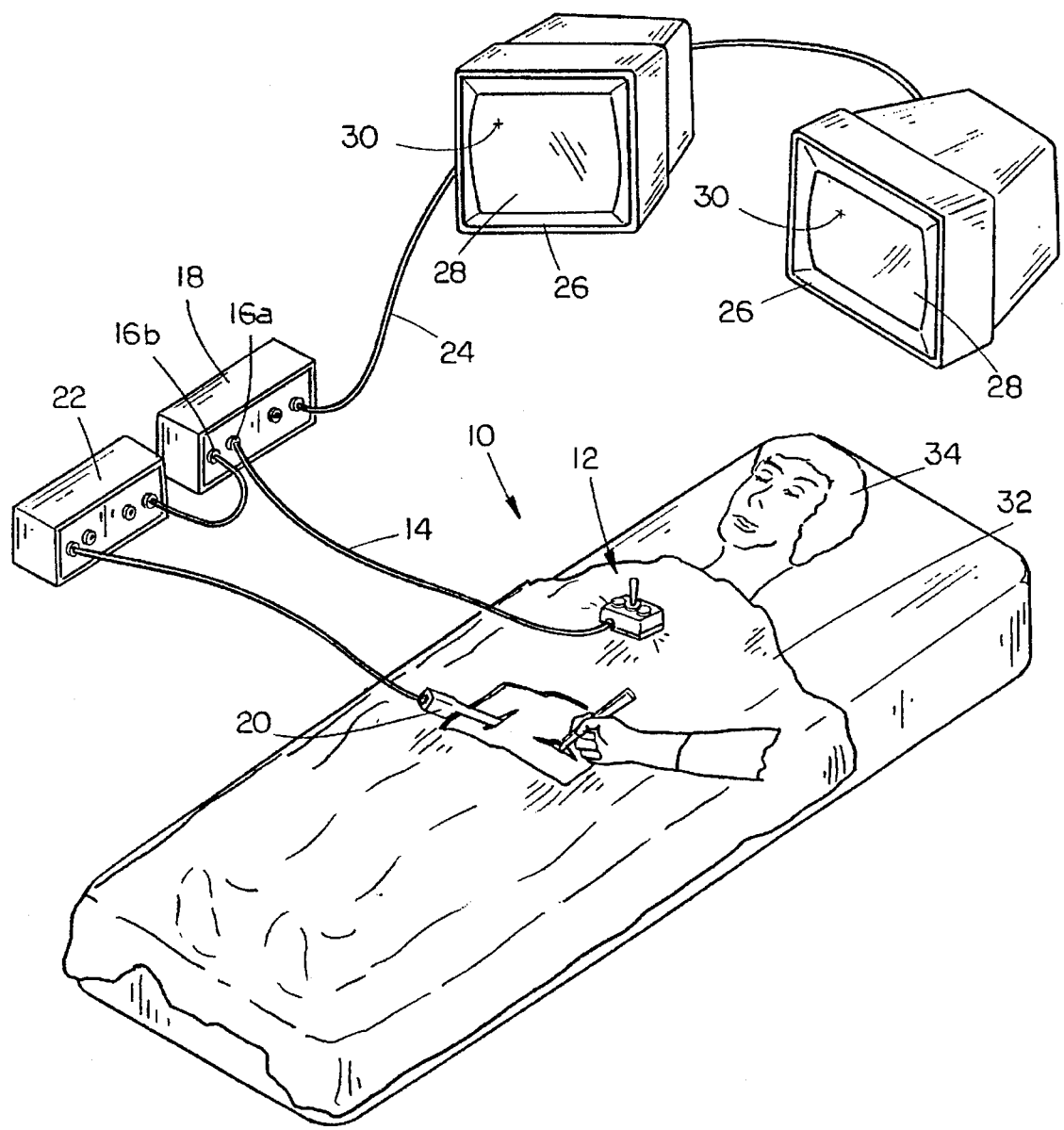
FIG. 1 is a pictorial view of a conventional surgical environment utilizing the cursor control apparatus of the present invention.

Referring now to the drawings, in which similar or corresponding parts are identified with the same reference numeral, and more particularly to FIG. 1, the cursor control apparatus of the present invention is designated generally at 10, and includes a conventional joystick mechanism 12 connected via electrical cable 14 to the input jack 16 of a conventional graphics generator device 18.

A conventional video camera 20, utilized in endoscopic surgery, is electrically connected to a camera box 22, which outputs a signal to a second input jack 16(b) in graphics generator device 18. The combined signals are then transmitted via cable 24 to video monitors 26 for viewing on the monitor screen 28. A cursor is depicked at 30 on screens 28, and is movable about the screen utilizing joystick mechanism 12, as described in more detail hereinbelow.

Cursor control apparatus 10 is preferably operable with only one hand, and therefore must be secured to the conventional drape 32 covering the patient 34.

Figure 2:
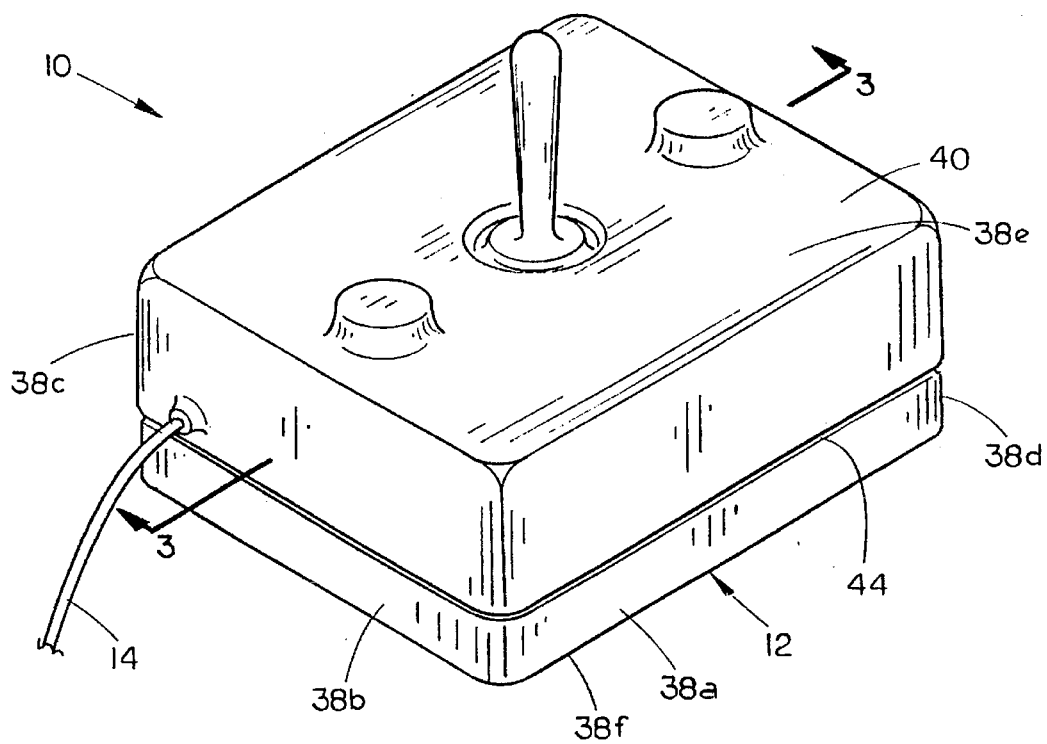
FIG. 2 is an enlarged perspective view of a first embodiment of the cursor control apparatus.
Figure 3:
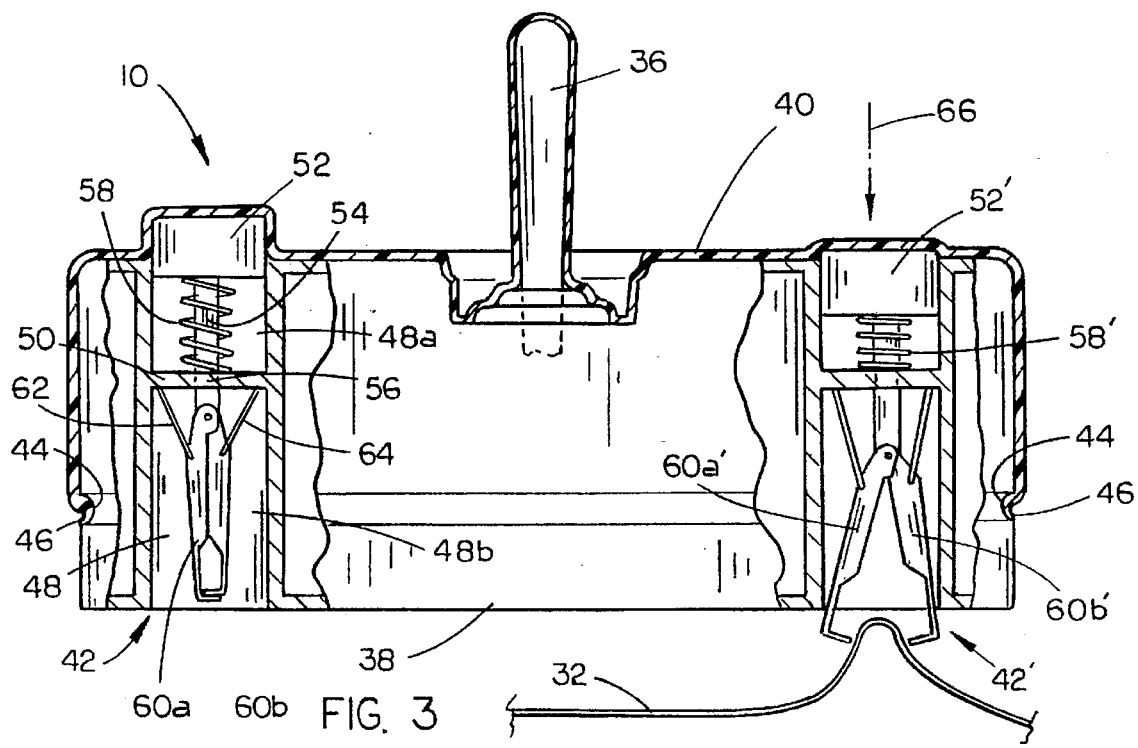
FIG. 3 is a sectional view taken at lines 3—3 in FIG. 2.

Referring now to FIGS. 2 and 3, one embodiment of the cursor control apparatus 10 includes a conventional joystick mechanism 12 of the type having an operable joystick 36 mounted on a housing 38. While the mechanical and electrical aspects of joystick mechanism 12 are conventional, the inventor has modified joystick mechanism 12 by adding a covering 40 and securement apparatus 42, which permit mechanism 12 to be sterilized, and to permit securement of mechanism 12 to drape 32.

As shown in FIG. 2, housing 38 includes four vertical sides 38a, 38b, 38c and 38d, a top surface 38e and a bottom surface 38f. A groove 44 is formed in each of the vertical sides 38a, 38b, 38c and 38d, so as to form a continuous peripheral groove. A synthetic molded covering 40 is mounted to all exposed upper surfaces of housing 38, joystick 36, and any projecting portions of securement apparatus 42, as shown in FIG. 3. Covering 40 may be of silicone, or other flexible material which permits operation of joystick 36, yet permits sterilization by heat, chemical bath and/or gaseous techniques. The covering 40 is cuffed into groove 44 and a sealant 46 applied along the entire extent of peripheral groove 44.

FIG. 3 shows one embodiment of a securement apparatus 42 which will permit selective securement of cursor control apparatus 10 to a drape 32 covering a patient. Each securement apparatus 42 preferably includes a vertical aperture 48 formed through housing 32 with a central horizontal wall 50 dividing aperture 48 into an upper portion 48a and a lower portion 48b. A push button 52 is mounted to the upper end of a shaft which projects through an aperture 56 in wall 50, to permit vertical movement of button 52 in upper portion 48a of aperture 48. A spring 58 biases button 52 upwardly from wall 50.

A pair of jaw members 60 are pivotally connected to the lower end of shaft 54 to permit pivotal movement of jaw members 60 towards and away from one another. A link 62 connects jaw member 60a to wall 50, while a link 64 connects jaw member 6b to wall 50 diametric of the connection of link 62. Links 62 and 64 are disposed such that vertical movement of shaft 54 will cause jaw member 60a and 60b to pivot about their connection to shaft 54 by virtue of links 62 and 64, as demonstrated by securement apparatus 42'. Thus, depressing button 52', as shown by arrow 66, will open jaws 60a' and 60b' to receive a portion of drape 32 therebetween. Permitting spring 58' to raise button 52' will cause jaw member 60a' and 60b' to grip drape 32 therebetween.

Figure 4:
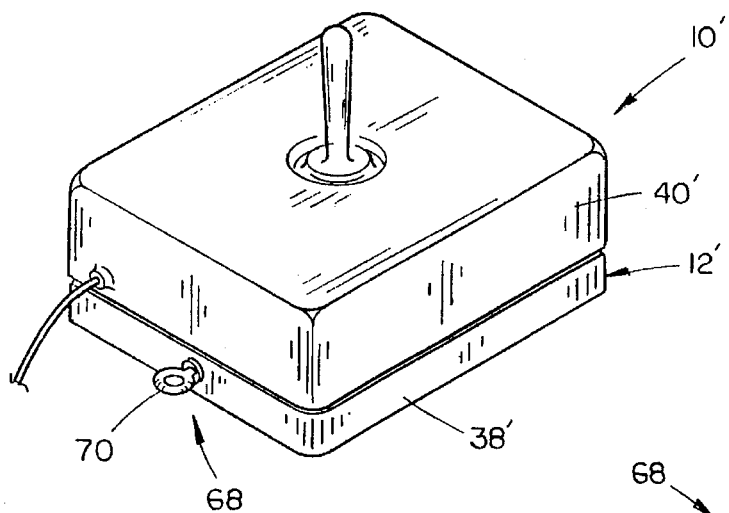
FIG. 4 is an enlarged perspective view of a second embodiment of the invention.
Figure 5:
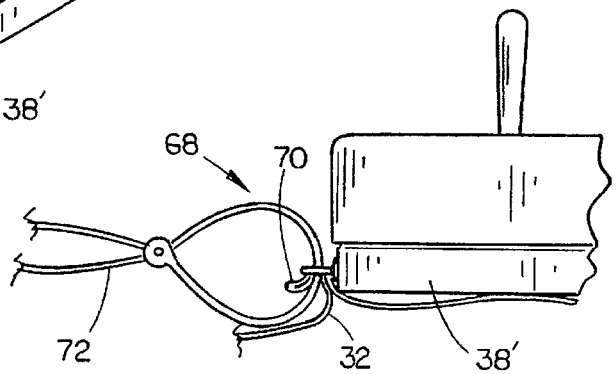
FIG. 5 is a side elevational view of the embodiment of FIG. 4.

Referring now to FIGS. 4 and 5, a second embodiment of the cursor control apparatus is designated generally at 10', and includes a conventional joystick mechanism 12' and the same covering 40' of the first embodiment. In the second embodiment of the invention, a securement apparatus 68 includes a ring 70 mounted to one side of housing 38'. As shown in FIG. 5, a conventional towel clamp 72 is utilized to grasp a portion of drape 32 and secure it through ring 70.

Figure 6:
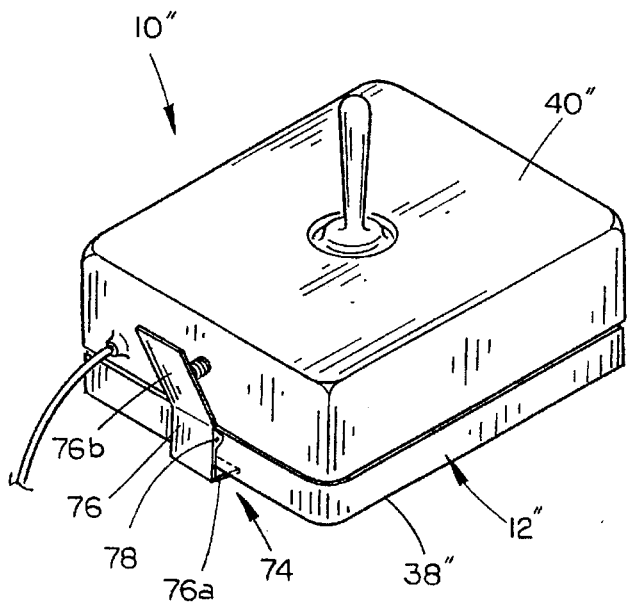
FIG. 6 is an enlarged perspective view of the third embodiment of the invention.
Figure 7:
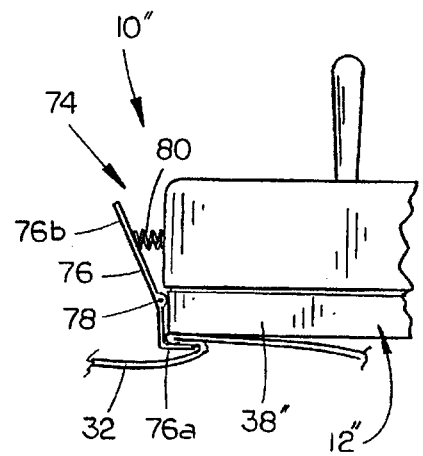
FIG. 7 is a side elevational view of the embodiment of FIG. 6.

A third embodiment of the invention is designated generally at 10" in FIGS. 6 and 7. Cursor control apparatus 10" includes a conventional joystick mechanism 12" and the same covering 40" as the first embodiment of the invention. The securement apparatus 74 of the third embodiment of cursor control apparatus 10" includes a lever 76 pivotally secured intermediate its upper and lower ends at a hinge 78 on one side of housing 38". The lower end of lever 76 is bent generally horizontal to form a leg 76a which will grip a portion of drape 32 between leg 76a and the bottom of housing 38". The upper end 76b of lever 76 is bent outwardly away from housing 38" at approximately the location of hinge 78. A spring 80 is mounted between upper end 76b and housing 38" to bias the lever upper end 76b away from housing 38', thereby producing a gripping force of leg 76a against the bottom of housing 38"

In operation, the cursor control apparatus 10 may be sterilized in any conventional manner, by virtue of the heat resistant, water-tight covering 40, encasing the upper half of the mechanism. The cursor control apparatus is then secured to the drape covering the patient in any one of the various methods described in FIGS. 3, 5, and 7 such that the cursor control apparatus is retained in position on the drape. Cable 14 is connected to graphics generator device 18, and camera 20 is connected to camera box 22 and device 18, in a conventional fashion. In use, movement of the joystick will move the cursor 30, as shown in FIG. 1, on the video screen 28 so as to precisely locate desired information on the monitor 26. The surgeon may cause cursor 30 to be moved with only one hand, and without requiring activity which could attract dirt or bacteria to the surgeon's hands.

Figure 8:
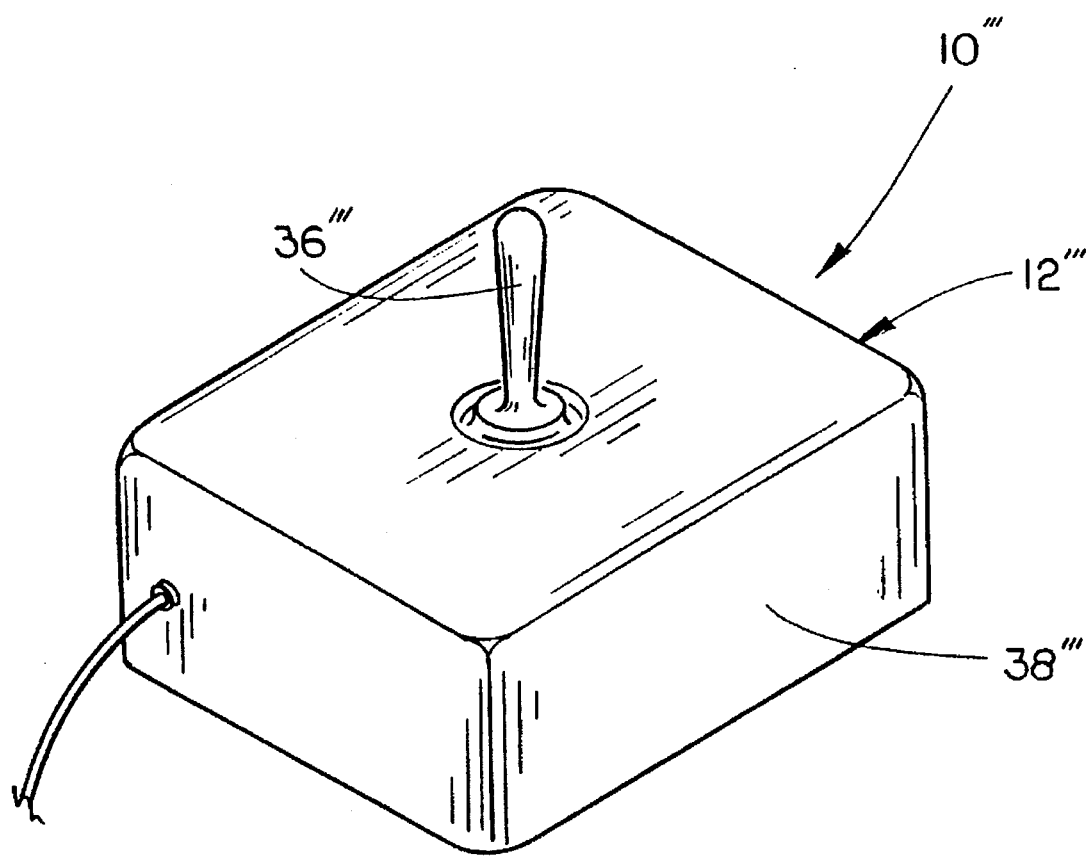
FIG. 8 is an enlarged perspective view of a fourth embodiment.

Referring now to FIG. 8, a third embodiment of the invention is designated generally at 10'''. This version of the control apparatus utilizes a housing 38''' which is completely sterilizable. This can be accomplished by utilizing sterilizable components within housing 38''', including joystick 36''', or by sealing the housing 38''' so that only the exterior of the housing need be sterilized.

Whereas the invention has been shown and described in connection with the preferred embodiments thereof, it will be understood that many modifications, substitutions and additions may be made which are within the intended broad scope of the appended claims. There has therefore been shown and described an improved cursor control apparatus which accomplishes at least all of the above stated objects.

I claim:

1. In combination:

a video camera electrically connected to a video monitor to display video received by the camera;

a cursor generating means electrically connected to said monitor to overlay a cursor indicator on the video display, said cursor indicator being operable independently of the video display on the monitor;

a cursor control apparatus located remotely from the monitor and generating means and in operable communication therewith;

operable control means on said cursor control apparatus, operable to cause movement of the cursor on the video display independent of the video display; and said cursor control apparatus having a resilient, flexible covering over the control means of a material which is sterilizable and permits operation of the control means.

2. The combination of claim 1, wherein said control apparatus includes a housing having a top surface, with said control means mounted on the top surface, and wherein said covering covers the entire top surface.

3. The combination of claim 1, wherein said cursor control apparatus is electrically connected to said video monitor to enable operable communication therewith.

4. The combination of claim 1, further comprising:

said cursor control apparatus including a housing; and means on said housing for selectively and removably securing the cursor control apparatus in position on a sheet material.

5. The combination of claim 4, wherein said securing means includes:

clamp means having a jaw member for gripping a portion of said sheet material; and said jaw member operably connected to said housing for movement between a clamped and an unclamped position.

6. The combination of claim 5, wherein said clamp means includes means for biasing said jaw member into the clamped position.

7. In combination:

a video camera electrically connected to a video monitor to display video received by the camera;

a cursor generating means electrically connected to said monitor to overlay a cursor indicator on the video display, said cursor indicator being operable independently of the video display on the monitor;

a cursor control apparatus located remotely from the monitor and generating means and in operable communication therewith;

operable control means on said cursor control apparatus, operable to cause movement of the cursor on the video display independent of the video display; and means on said cursor control apparatus for selectively and removably securing the cursor control apparatus in position on a sheet material.

8. The combination of claim 7, wherein said cursor control apparatus includes a housing, and wherein said securing means includes:

clamp means having a jaw member for gripping a portion of said sheet material; and said jaw member operably connected to said housing for movement between a clamped and unclamped position.

9. The combination of claim 8, wherein said clamp means includes means for biasing said jaw member into the clamped position.

10. A cursor control apparatus for remotely moving a cursor depicted on a video monitor, comprising:

a housing with operable control means thereon for moving said cursor on the video monitor independently of any video display on the monitor;

said housing having a resilient flexible covering over the control means, of a material which is sterilizable and permits operation of the control means; and means on said housing for selectively and removably securing the housing in position on a sheet material.

11. In combination:

a video camera electrically connected to a video monitor to display video received by the camera;

a cursor generating means electrically connected to said monitor to overlay a cursor indicator on the video display, said cursor indicator being operable independently of the video display on the monitor;

a cursor control apparatus located remotely from the monitor and generating means and in operable communication therewith;

operable control means on said cursor control apparatus, operable to cause movement of the cursor on the video display independent of the video display; and said control means and cursor control apparatus being formed entirely of components of sterilizable materials.

12. A method for indicating a location on a video display in a sterile environment wherein the sterile environment includes a sterile work location, a video camera connected to a video monitor to display video received by the camera, a cursor generator connected to the monitor to overlay a cursor indicator on the video display, a cursor control apparatus connected to the cursor generator to move the cursor indicated on the monitor independently of the video display, comprising the steps of:

positioning and operating the video camera at the work location to display selected portions of the work location on the monitor;

positioning the control apparatus remotely of the monitor;

removably attaching the control apparatus to the work location; and a person working at the work location manipulating the cursor control apparatus so as to move the cursor indicator on the screen independently of the video display, said manipulating step including manipulating a joystick on the control apparatus.

13. The method of claim 12, wherein the sterile environment is a surgical theater with a patient positioned under a sterile sheet, and wherein the step of removably attaching the control apparatus includes the step of removably attaching the control apparatus to the sheet.

* * * * *